United States Patent
Kerber

(10) Patent No.: US 8,858,593 B2
(45) Date of Patent: Oct. 14, 2014

(54) EMERGENCY WOUND TREATMENT DEVICE AND METHOD

(75) Inventor: Charles W. Kerber, La Mesa, CA (US)

(73) Assignee: Charles W. Kerber, M.D., Inc., La Mesa, CA (US)

( * ) Notice: Subject to any disclaimer, the term of this patent is extended or adjusted under 35 U.S.C. 154(b) by 323 days.

(21) Appl. No.: 13/354,227

(22) Filed: Jan. 19, 2012

(65) Prior Publication Data

US 2012/0191129 A1      Jul. 26, 2012

Related U.S. Application Data

(60) Provisional application No. 61/436,562, filed on Jan. 26, 2011.

(51) Int. Cl.
*A61B 17/03*  (2006.01)
*A61B 19/00*  (2006.01)
*A61B 17/00*  (2006.01)

(52) U.S. Cl.
CPC ....... *A61B 17/0057* (2013.01); *A61B 2019/303* (2013.01); *A61B 2017/00893* (2013.01); *A61B 2017/00884* (2013.01); *A61B 2017/00889* (2013.01); *A61B 2017/00898* (2013.01); *A61B 2017/00623* (2013.01)
USPC ............. 606/213; 606/214; 606/215; 604/59; 604/60; 604/61

(58) Field of Classification Search
CPC ................. A61B 17/0057; A61B 2017/00623; A61B 2017/00884; A61B 2017/00889; A61B 2017/00893; A61B 2017/00898; A61B 2019/303; A61B 19/026
USPC ......................... 606/213–215, 232, 191–194; 604/59–61; 401/133–134
See application file for complete search history.

(56) References Cited

U.S. PATENT DOCUMENTS

| 682,090 | A | | 10/1901 | Lee | |
|---|---|---|---|---|---|
| 5,310,407 | A | * | 5/1994 | Casale | 604/506 |
| 5,419,765 | A | | 5/1995 | Weldon et al. | |
| 5,549,633 | A | * | 8/1996 | Evans et al. | 606/139 |
| 6,027,471 | A | * | 2/2000 | Fallon et al. | 604/59 |
| 6,475,177 | B1 | * | 11/2002 | Suzuki | 604/11 |
| 6,589,269 | B2 | | 7/2003 | Zhu et al. | |
| 6,849,082 | B2 | * | 2/2005 | Azevedo | 606/214 |
| 7,371,403 | B2 | | 5/2008 | McCarthy et al. | |
| 7,943,810 | B2 | | 5/2011 | Buckman et al. | |
| 2009/0324319 | A1 | * | 12/2009 | Houde et al. | 401/138 |
| 2011/0077682 | A1 | * | 3/2011 | Gregory et al. | 606/213 |

* cited by examiner

*Primary Examiner* — Julian W Woo
*Assistant Examiner* — Lucas Paez
(74) *Attorney, Agent, or Firm* — Gary L. Loomis; G. L. Loomis & Associates Inc

(57) ABSTRACT

An emergency medical device and method is provided for treatment of open wounds by enhancing clotting and arresting hemorrhaging, particularly in the area of the neck, abdomen, chest or groin. The devices includes an elongated delivery tube for insertion into a wound cavity and subsequent delivery of a space filling, sponge-like mass containing a polymerizable liquid sealant that polymerizes upon contact with body fluids after which the delivery tube is removed.

16 Claims, 4 Drawing Sheets

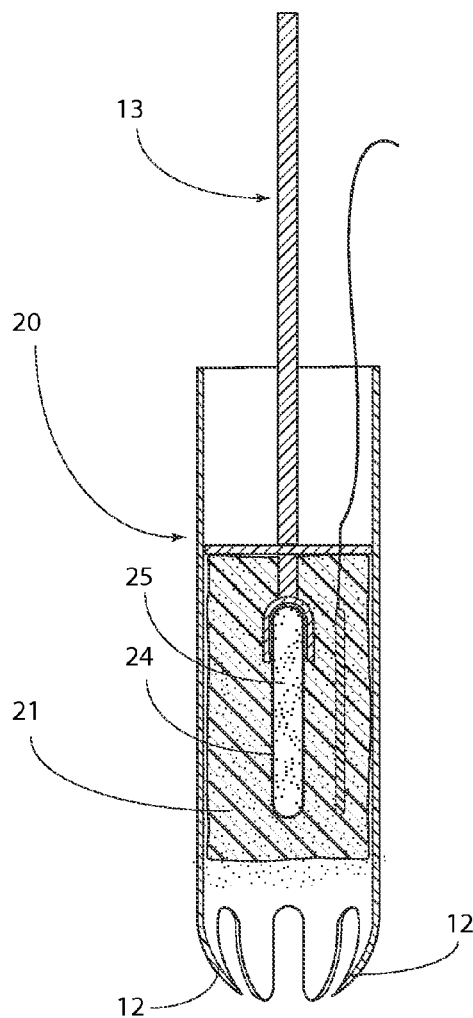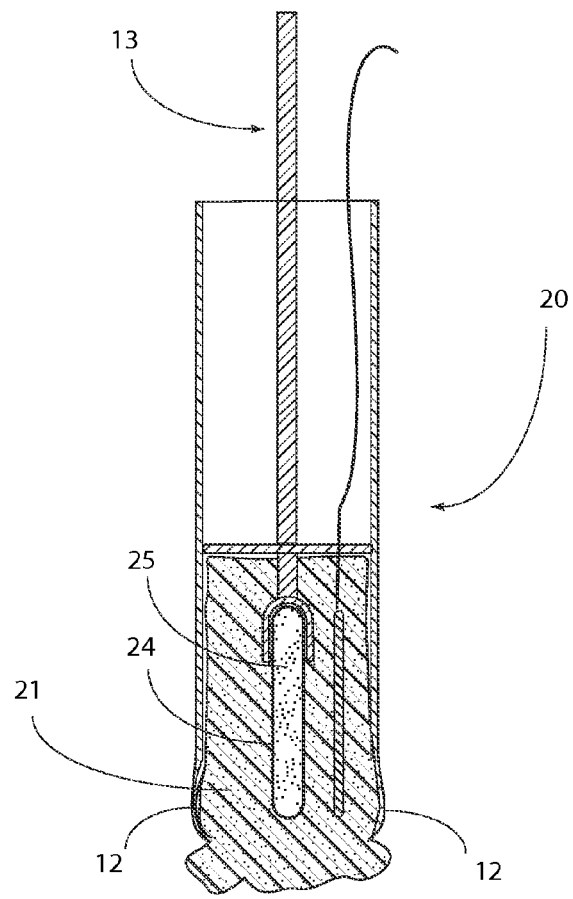
FIG. 3
FIG. 4

EMERGENCY WOUND TREATMENT DEVICE AND METHOD

CROSS-REFERENCE TO RELATED APPLICATION

This application claims priority under 35 U.S.C. §119(e) to U.S. Provisional Application No. 61/436,562 filed Jan. 26, 2011, which is herein incorporated by reference.

FIELD OF THE INVENTION

The field of this invention is medical treatment of open wounds in emergency circumstances such as combat and accident situations.

BACKGROUND

Medically useful liquid tissue adhesives and sealant composition are known in the art, however delivery of such compositions for sealing open and deep wounds, principally in the area of the neck, abdomen, chest or groin, is difficult. The ability to quickly and easily treat wounds is particularly pertinent in emergency situations such as a battlefield or an accident scene, since in such life or death situations, it is essential to stop bleeding and prevent hemorrhage to allow for evacuation of the patient. An ideal device must be self-contained, lightweight, and easily utilized by individuals with minimal medical training.

Various devices and methods for control of severe bleeding are known in the art. For example, U.S. Pat. No. 7,943,810 to Buckman et al. describes devices and methods for achieving hemostasis in patients who have received skin-penetrating wounds to the periphery, including the head, arms, and legs. The devices utilize fluid impermeable barriers surrounded by exterior dams and pressure to achieve tamponade and hemostasis, primarily by exertion of force to hold the dams against the skin surrounding a wound. Such devices do not utilize adhesives to function as they are attached to the patient using mechanical locking devices.

U.S. Pat. No. 5,419,765 to Weldon et al. describes a wound-treating device, which is adapted to treat wounds, and particularly to enhance clotting of wounds in blood vessels. The wound-treating device includes an elongated tube comprising at least two lumens wherein one of the lumens is attached to a flow control device partially positioned within the blood vessel to provide local flow control and an inflatable means, such as a flexible membrane is deliverable through the other lumen. Such a device provides a means for depositing a hemostatic agent in the opening of a blood vessel.

U.S. Pat. No. 6,589,269 to Zhu et al. describes a patch applicator requiring a source of vacuum to administer a patch on top of and over a wound in tissue, followed by subsequent delivery of a flowable adhesive onto the patch and tissue surrounding the patch. Such a system is not suitable for use in most emergency situations.

While U.S. Pat. No. 7,371,403 to McCarthy et al. describes hemorrhage control wound dressings, and methods for their use, wherein the wound dressings are formed of a material comprising chitosan, a hydrophilic polymer, a polyacrylic polymer or a combination thereof, no device is disclosed for utilization of the compositions in emergency medical situations Therefore, a need exists for a simple, portable device to stop bleeding and prevent hemorrhage in emergency medical situations.

A need also exists for device that is self-contained, lightweight, and easily utilized by individuals with minimal medical training.

A further need exists for a device applicable to life or death situations to stop bleeding and to allow for evacuation of the patient.

The present invention addressed these and other needs.

SUMMARY OF THE INVENTION

The present invention discloses devices and methods for the introduction of medically useful polymerizable liquid tissue-adhesives, wound sealants and hemostatic agents into open wounds of a human body, particularly in the neck, abdomen, chest and groin areas. The devices and methods presented herein are particularly suitable for use in emergency medical situations such as those occurring on battlefields and at accident scenes to prevent hemorrhage and to seal the wounds to prevent infection thus allowing for the transport of the patient.

Certain preferred embodiments of the device have a delivery component and a wound control component. The delivery component consists of an elongated tube with a proximal open end and a distal open end and a plunger mechanism disposed therein. The plunger mechanism has a rod element and a disc element wherein the disk element has a diameter smaller that the luminal diameter of the elongated tube and is fixedly attached to and circumferentially disposed about the rod element such that the plane of the disc element is perpendicular to the longitudinal axis of elongated tube and wherein the disc element of the plunger mechanism is disposed within the lumen of the elongated tube. The wound control component comprises compressible and expandable sponge-like material disposed in a compressed state within the lumen of the elongated tube between the plunger disc element and the distal end of the elongated tube such that depression of the plunger mechanism expels the compressed sponge-like material from the distal end of the elongated tube wherein the sponge-like material expands in the wound. A break-seal vessel such as a vial or ampoule containing a liquid composition that polymerizes upon contact with body fluids is disposed within the compressible and expandable sponge-like material, wherein the break-seal vessel is positioned and configured to maintain contact with the distal end of the rod element of the plunger mechanism such that certain controlled movements of the rod element effect the breaking of the break-seal vessel and release of the polymerizable liquid composition therein.

In a typical emergency procedure, the distal end of the device is inserted into an open wound and maneuvered into a desired position within the wound wherein the plunger mechanism is depressed to expel the sponge-like material, containing the a break-seal vial or ampoule of polymerizable liquid composition, expands within the wound, after which the rod of the plunger mechanism is flexed or moved to effect breakage of the break-seal vial or ampoule to release the polymerizable composition which diffuses throughout the sponge-like material. The elongated tube, together with the plunger mechanism, is then removed from the wound wherein the polymerizable liquid composition polymerizes upon contact with blood or other body fluids to seal the wound.

In certain preferred embodiments the device further comprise a string or cord having a distal end disposed within and fixedly attached to the sponge-like material and a proximal end extending through the lumen and exiting from the open proximal end of elongated tube. In certain preferred embodiments the distal end of the string or chord comprises a radiopaque marker which functions to allow subsequent instrumental visualization and aids in removal of the emergency device to facilitate further medical procedures.

In certain other preferred embodiments wherein the elongated tube is fabricated from a suitably resilient material such as a moderately flexible plastic, the distal end of elongated tube is dome shaped and comprises a plurality of flexible curvilinear dome segments positioned circumferentially and extending axially. In such embodiments such that the dome segments spread apart are as contents of tube are expelled. Such a dome shaped distal end aids is the smooth insertion of the device into a wound.

In certain other embodiments the distl end of the rod element is provided with a suitable gripping means such as a tab, a ball, an element with one or more finger holes and the like to aid in the depression and retraction of the plunger mechanism.

BRIEF DESCRIPTION OF THE DRAWINGS

FIG. 3 is a cut-away frontal orthogonal view of an embodiment of a complete device of the present invention.

FIG. 4 depicts the embodiment of FIG. 3 wherein the plunger has been partially depressed.

DETAILED DESCRIPTION OF THE INVENTION

Figure 1:
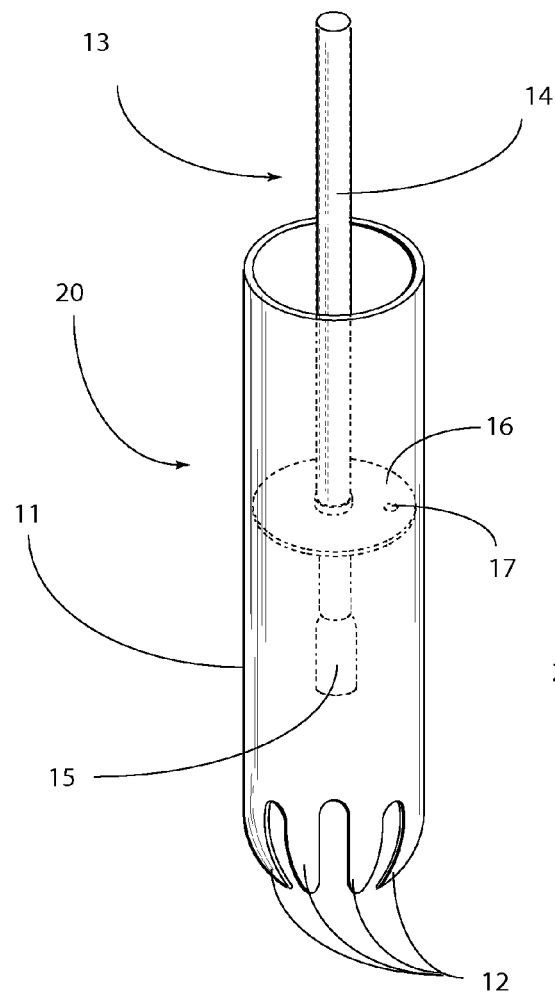
FIG. 1 is an isometric view depicting certain elements of a device of the present invention.

FIGS. 1-6 illustrate a typical embodiment of an emergency wound treatment device of the present invention. In FIG. 1 is depicted certain components of an embodiment of a wound treatment device 20 comprising an open-ended elongated tube 11 wherein a dome shaped distal end comprises a plurality of flexible curvilinear dome segments 12 positioned circumferentially and extending axially; such that the dome segments 12 spread apart are as contents of tube 11 are expelled. The embodiment of FIG. 1 is provided with a plunger mechanism 13 comprising a rod element 14 and a disc element 16 wherein the disk element has a diameter slightly smaller that the luminal diameter of the elongated tube 11 and is fixedly attached to and circumferentially disposed about the rod element 14 such that the plane of the disc element 16 is perpendicular to the longitudinal axis of elongated tube 11. By this arrangement the disc element 16 of the plunger mechanism 13 is slidably movable within the lumen of the elongated tube 11 as the rod element 14 is depressed into or retracted from the elongated tube.

Figure 2:
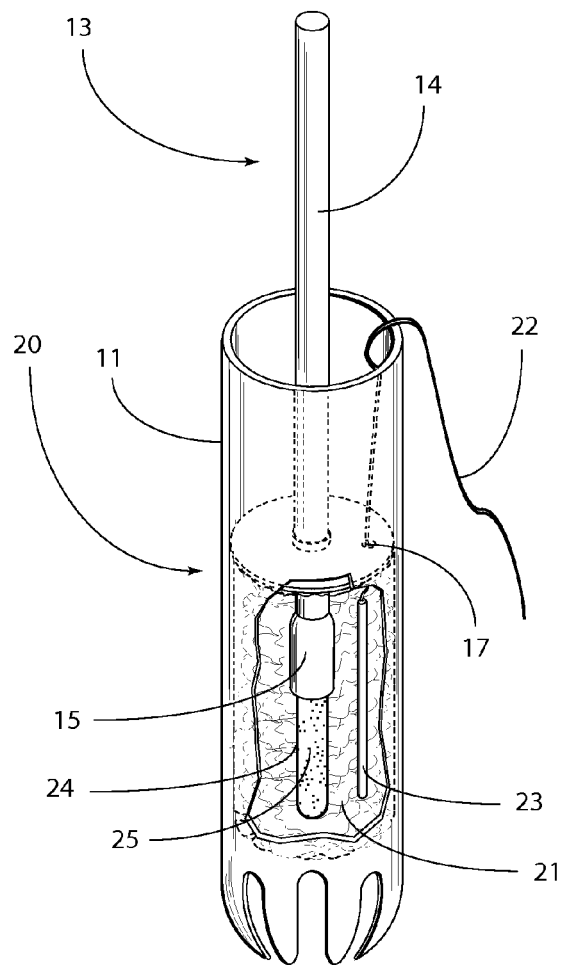
FIG. 2 is an isometric view depicting a complete device of the present invention.

In FIG. 2 is depicted the complete emergency wound treatment device 20, wherein a compressible and expandable open-cell sponge-like material 21 is disposed in a compressed configuration within the lumen of the elongated tube 11 between the plunger disc element 16 and the distal end of the elongated tube 11 such that the distal movement of the plunger mechanism 13 expels the expandable sponge-like material 21 from the distal end of the elongated tube 11. A break-seal vessel 24 filled with a polymerizable liquid composition 25 is disposed within the sponge-like material 21. In this embodiment the distal end of the rod element 14 comprises a hollow shell element 15, which is open at the distal end and is sized to accept a portion of a break-seal ampoule 24 and wherein a portion of the break-seal ampoule 24 is disposed within the open distal end of the hollow shell element 15 such that controlled movements of the rod element 14 effect breakage of the break-seal vessel 24 and concomitant release of the polymerizable liquid composition 25 therein.

Figure 5:
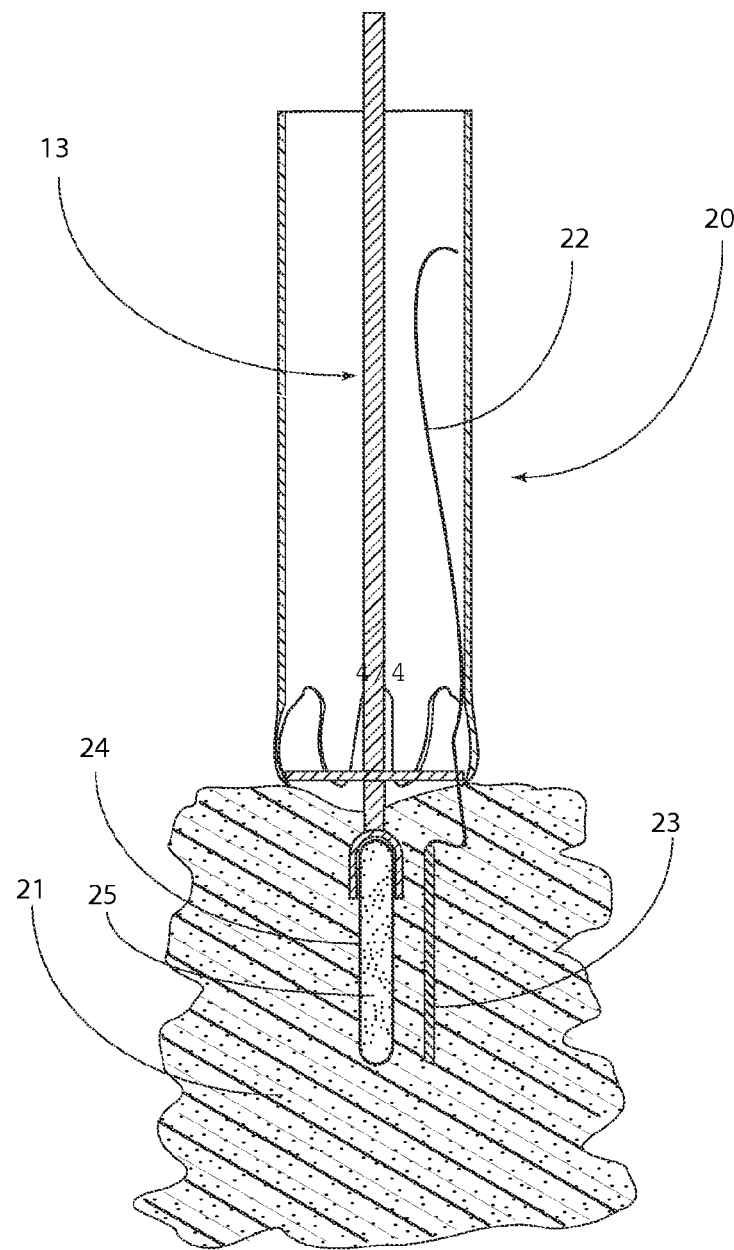
FIG. 5 depicts the embodiment of FIG. 3 wherein the plunger has been completely depressed.

In FIG. 3 is depicted a sectional view of the complete emergency wound treatment device 20 as depicted in FIG. 2. FIG. 4 depicts a sectional view of the complete emergency wound treatment device 20 depicted in FIG. 2 wherein the plunger mechanism 13 has been partially depressed such that the expandable sponge-like material 21, and contents thereof, is emerging from the distal end of the elongated tube 11 as the dome segments 12 are spread apart to permit expulsion and concurrent expansion of the sponge-like material 21 and contents thereof. FIG. 5 depicts a sectional view of the complete emergency wound treatment device 20 as depicted in FIGS. 3 and 4 wherein the plunger mechanism 13 has been fully depressed so that the sponge-like material 21, and contents thereof, is fully emerged from the distal end of the elongated tube 11 and wherein the sponge-like material 21 is fully expanded.

Figure 6:
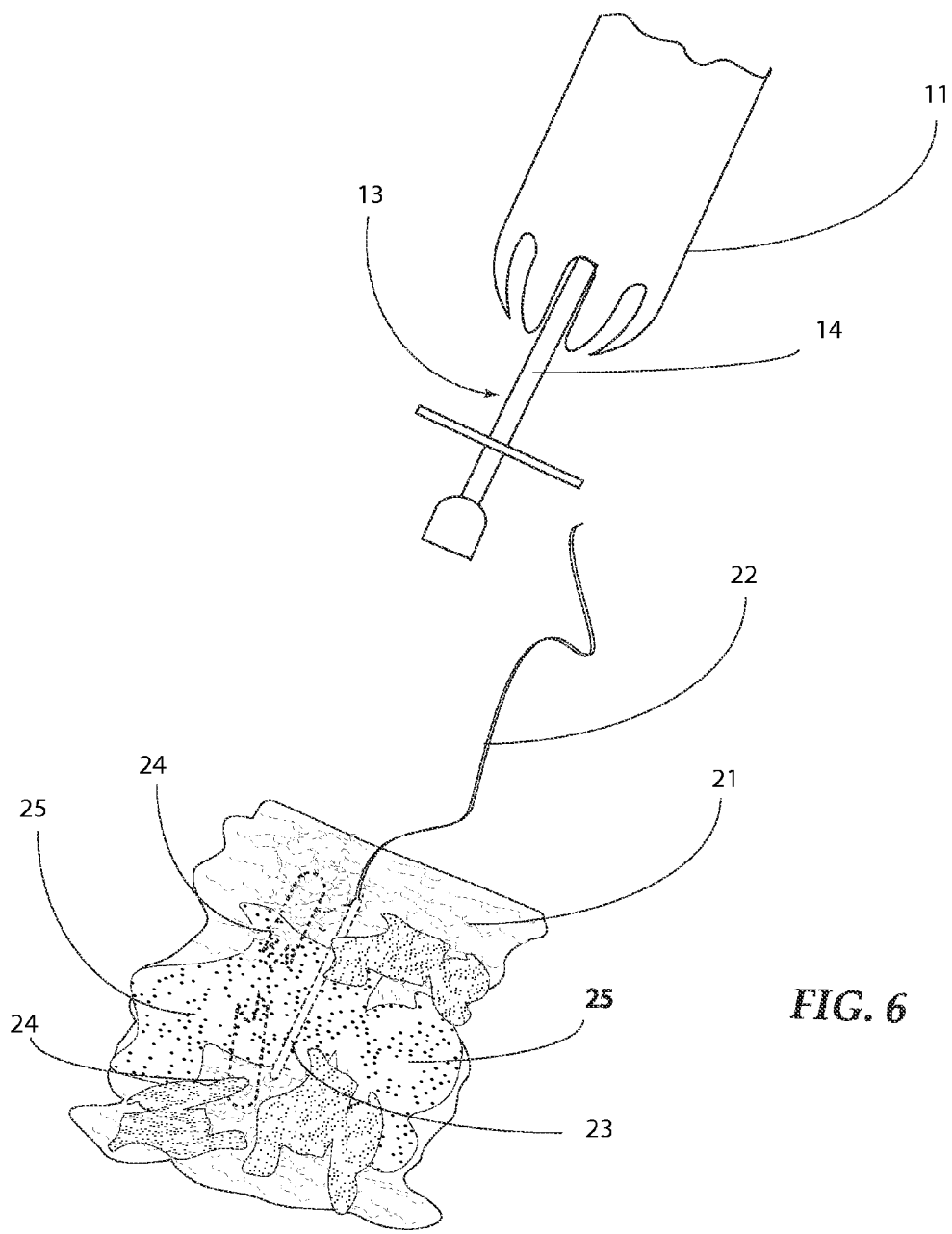
FIG. 6 depicts the embodiment of FIG. 3 wherein the sponge-like material has been deployed and the polymerizable composition therein has been released.

FIG. 6 illustrates a sectional view of the expelled and expanded sponge-like material 21 wherein the break-seal ampoule 24 has been broken by the controlled movement of rod element 14 to release polymerizable liquid composition 25 which has diffused throughout the sponge-like material 21 and polymerizes upon contact with blood and/or other body fluids in the wound into which it has been inserted. As is depicted in FIG. 6, in this procedure the elongated tube 11 and the plunger mechanism 13 are completely withdrawn from the wound (as shown) immediately after break-seal vessel 24 has been broken.

Additionally, in the embodiment depicted in FIGS. 1-6 the disc element 16 comprises an optional aperture 17 through which is disposed an optional cord or string 22 the distal end of which comprises an optional radiopaque marker 23 disposed within the sponge-like material 21. During the procedure, the polymerization of the liquid composition 25 effects fixation of the distal portion of cord or string 22 and the radiopaque marker 23 within the sponge-like material 21. The radiopaque marker, as well as the cord or string, function to aid removal of the sponge-like material 21 in subsequent medical procedures.

While in the embodiment depicted in FIGS. 1-6 the distal end of the rod element 14 comprises a hollow shell element 15 to maintain contact with the break-seal ampoule 24 such that controlled movements of the rod element 14 effect breakage of the break-seal ampoule 24 and concomitant release of the polymerizable liquid composition 25 therein, the invention is not limited by this embodiment. In certain other embodiments the break-seal vessel may be attached to the distal end of a rod element by various means including, but not limited to gluing, fusing, and tying with thread or wire.

If necessary, multiple devices can be deployed in a procedure to treat a single wound. Additionally, the expandable sponge-like material may further comprise one or more various pharmaceutical agents or other biologically active substances including, but not limited to, thrombogenic agents, antipathogenic agents, antibiotics, antimicrobial agents, antiviral agents and the like.

In embodiments of the present invention suitable compressible/expandable sponge-like materials may include those materials common in surgical sponges or pads. In certain embodiments the sponge-like material comprises materials including, but not limited to, cotton gauze, non-woven textiles comprising cotton or synthetic fibers such as rayon and the like, cellulosics (cellulose, carboxymethyl cellulose, etc.), polyolefins, and the like. In certain other embodiments the sponge-like material is comprises a bioabsorbable materials including, but not limited to, polymers or copolymers of lactide, glycolide, caprolactone, polydioxanone, trimethylene carbonate, polyorthoesters, polyethylene oxide, collagen, chondroitin, chitin, hyaluronic acid and the like. The most desirable sponge-like materials for use in the present invention are pliable, compressible and expandable; and combine absorbency with capillarity properties.

Useful polymerizable liquid compositions suitable for use in the present invention include medical tissue adhesives and sealant compositions comprising polymerizable monomers, oligomers or pre-polymers that may be anionically polymerizable, free radical polymerizable, or polymerizable by zwitterions or ion pairs. In such systems the liquid monomers oligomers or pre-polymers polymerize upon contact with body fluids such as blood resulting in the in situ formation of a solid polymer. In certain embodiments such medically useful tissue adhesives and sealant compositions include, but are not limited to, those comprised of polymerizable monomers such as 2-cyanoacrylates including alkyl 2-cyanoacrylates and alkoxyalky 2-cyanoacrylates; dialkylmethylene malonates, as well as oligomers or pre-polymers thereof. Also useful are cyanoacrylate-capped heterochain polymers, comprising one or more oxyalkylene, alkylene carbonate, and ester-units derived from cyclic lactones. Particularly suitable polymerizable liquid compositions include, but not limited to, those described in U.S. Pat. No. 6,224,622; U.S. Pat. No. 3,559,652; U.S. Pat. No. 5,624,669; U.S. Pat. No. 5,417,352; U.S. Pat. No. 6,538,026; U.S. Pat. No. 6,476,070; U.S. Pat. No. 5,306,490; and U.S. Pat. No. 5,403,591 as well as references cited therein, which are all herein included by way of reference.

Suitable materials for the fabrication of the elongated tubes and plunger rods of the present invention include, but are not limited to, known biocompatible plastics, plastic composites, cardboard and metals. In embodiments wherein the distal end of elongated tube is dome shaped and comprises a plurality of flexible curvilinear dome segments positioned circumferentially and extending axially, the elongated tube is fabricated from a suitably resilient material such as a moderately flexible plastic including, but not limited to, polyethylene, polypropylene, PVC, and the like.

Suitable materials for fabrication of the plunger disc element include, but are not limited to, known biocompatible plastics, plastic composites, elastomers, pliable metals and the like.

Suitable materials for the break-seal vessels such as vials or ampoules include biocompatible glasses and plastics. Suitable break-seal vessels such as vials and ampoules are well known in the art and are available from numerous commercial sources such as James Alexander Corporation, Blairstown, N.J.

In the embodiments that utilize radiopaque markers, such markers may comprise suitable heavy metals including, but not limited to, gold, platinum, palladium, silver, tantalum, nickel-titanium alloy, iridium, rhenium, tungsten, rhodium, ruthenium, hafnium and the like. In certain preferred embodiments the radiopaque marker comprises gold or platinum.

All materials used in the devices should be sterilizable either as individual components or in an assembled device.

It is understood that the above-described embodiments are merely illustrative of the application. Other embodiments may be readily devised by those skilled in the art, which will embody the principles of the invention and fall within the spirit and scope thereof.

I claim:

1. A wound treatment device comprising:
    an elongated tube having an open proximal end, an open distal end, an outer surface, a luminal diameter and a luminal surface;
    a plunger mechanism comprising a rod element having a proximal end and a distal end and a disc element having an upper surface and a lower surface wherein the disc element has a diameter smaller that the luminal diameter of the elongated tube and is fixedly attached to and circumferentially disposed around the rod element such that the proximal end of the rod element is disposed above the upper surface of the disc element and the distal end of the rod element is disposed beneath the lower surface of the disc element and wherein the plane of the disc element is perpendicular to the longitudinal axis of the elongated tube, such the disc element of the plunger mechanism is slidably movable within the lumen of the elongated tube as the rod element is depressed into or retracted from the elongated tube;
    a compressible and expandable sponge-like material disposed in a compressed state within the lumen of the elongated tube between the disc element and the distal end of the elongated tube such that depression of the rod element of the plunger mechanism expels the expandable sponge-like material from the distal end of the elongated tube wherein the sponge-like material freely expands; and
    a break-seal vessel, containing a liquid composition that polymerizes upon contact with body fluids, disposed within the expandable sponge-like material, wherein the break-seal vessel is configured and positioned to maintain contact with the distal end of the rod element of the plunger mechanism such that certain controlled movements of the rod element effects breakage of the break-seal vessel and concomitant release of the polymerizable liquid composition.

2. The wound treatment device of claim 1 wherein the open distal end of the elongated tube is dome shaped and comprises a plurality of flexible curvilinear dome segments positioned circumferentially and extending axially such that the dome segments spread apart as the expandable sponge-like material is expelled from the elongated tube.

3. The wound treatment device of claim 1 wherein the liquid composition comprises a 2-cyanoacrylate.

4. The wound treatment device of claim 3 wherein the 2-cyanoacrylate is an alkyl 2-cyanoacrylate or alkoxyalky 2-cyanoacrylate.

5. The wound treatment device of claim 1 wherein the compressible and expandable sponge-like material further comprises a pharmaceutically active agent.

6. The wound treatment device of claim 5 wherein the pharmaceutically active agent is selected from the group consisting of hemostatic agents, thrombogenic agents, antipathogenic agents, antibiotics, antimicrobial agents and antiviral agents.

7. The wound treatment device of claim 5 wherein the pharmaceutically active agent is a hemostatic agent.

8. The wound treatment device of claim 1 further comprising a radiopaque marker disposed within the compressible and expandable sponge-like material.

9. The wound treatment device of claim 1 further comprising a cord extending through the lumen of the elongated tube from the distal end to a point within the compressible and expandable material.

10. The wound treatment device of claim 8 wherein the radiopaque marker is fixedly attached to a cord extending through the lumen of the elongated tube from the distal end to a point within the compressible and expandable material.

11. The wound treatment device of claim 1 wherein the elongated tube, the disc element and the rod element are fabricated from a plastic.

12. The wound treatment device of claim 1 wherein the rod element is fabricated from a plastic.

13. The wound treatment device of claim 1 wherein the disc element is fabricated from a plastic.

14. A procedure for emergency wound treatment comprising:
   (a) inserting the distal end of the elongated tube of a device of claim 1 into an open wound;
   (b) depressing the proximal end of the rod element until the compressible and expandable sponge-like material and contents therein has been completely expelled from the elongated tube;
   (c) executing suitable movements of the rod element to effect breakage of the break-seal vessel resulting in the release of the polymerizable liquid composition;
   (d) removing elongated tube and plunger mechanism from the open wound.

15. The wound treatment device of claim 1 wherein the distal end of the rod element comprises a hollow open-ended shell element which is sized and configured such that a portion of the break-seal vessel can be disposed therein.

16. The wound treatment device of claim 1 wherein the distal end of the rod element is fixedly attached to the break-seal vessel.

* * * * *